US008287513B2

(12) United States Patent
Ellstrom et al.

(10) Patent No.: US 8,287,513 B2
(45) Date of Patent: Oct. 16, 2012

(54) PIERCING MEMBER PROTECTION DEVICE

(75) Inventors: Anna Ellstrom, Molndal (SE); Tobias Rosenquist, Kallered (SE)

(73) Assignee: Carmel Pharma AB, Gothenburg (SE)

( * ) Notice: Subject to any disclaimer, the term of this patent is extended or adjusted under 35 U.S.C. 154(b) by 679 days.

(21) Appl. No.: 11/853,388

(22) Filed: Sep. 11, 2007

(65) Prior Publication Data
US 2009/0069783 A1    Mar. 12, 2009

(51) Int. Cl.
*A61M 5/32* (2006.01)
*A61M 32/00* (2006.01)
*A61M 5/00* (2006.01)
*A61B 19/00* (2006.01)
*B65B 1/04* (2006.01)
*B65B 3/04* (2006.01)
*B65B 3/00* (2006.01)
*B65D 39/00* (2006.01)
*B65B 41/00* (2006.01)
*B65B 43/00* (2006.01)
*B65B 47/00* (2006.01)
*B65B 51/00* (2006.01)

(52) U.S. Cl. .......... 604/415; 604/82; 604/187; 604/403; 604/411; 604/414; 604/416; 141/97; 141/319; 141/329; 141/346; 141/369; 141/372; 141/373; 141/383; 141/386; 141/387; 215/247; 215/316

(58) Field of Classification Search .............. 604/82, 604/86, 87, 88, 89, 187, 246, 403, 411, 412, 604/414, 415, 905; 141/27, 97, 286, 319, 141/329, 346, 369, 372, 373, 383, 386, 387; 215/247, 316, DIG. 8; D24/127
See application file for complete search history.

(56) References Cited

U.S. PATENT DOCUMENTS

| 1,844,342 A | 2/1932 | Berman |
| 2,010,417 A | 8/1935 | Schwab |
| 2,697,438 A | 12/1954 | Hickey |

(Continued)

FOREIGN PATENT DOCUMENTS
AU    200112863    5/2003
(Continued)

OTHER PUBLICATIONS

Taiwan Search Report for Taiwan Patent Application 092106323 dated Mar. 21, 2003 (4 pages).

(Continued)

Primary Examiner — Tatyana Zalukaeva
Assistant Examiner — Adam Marcetich
(74) Attorney, Agent, or Firm — Diehl Servilla LLC

(57) ABSTRACT

A female piercing member protection device for connection with a male connection part, and a method for connecting the device to a male connection part. The device includes an outer casing and a connection member at least partly enclosed in the outer casing. The outer casing is moveable between first and second positions. In the first position, the connection member is substantially locked from movement along the longitudinal axis A, and in the second position the connection member is able to move along the longitudinal axis A. The device also has an activated position and an inactivated position. When the outer casing is in the second position, a deformable locking device is prevented from deformation by the outer casing to prevent disengagement of the male connection part. A secure piercing member protection device significantly minimizes the risk for a user to be exposed to contaminants and the piercing member itself.

19 Claims, 7 Drawing Sheets

U.S. PATENT DOCUMENTS

| | | | |
|---|---|---|---|
| 2,717,599 A | 9/1955 | Huber | |
| 3,064,651 A | 11/1962 | Henderson | |
| 3,071,135 A | 1/1963 | Baldwin et al. | |
| 3,308,822 A | 3/1967 | DeLuca | |
| 3,316,908 A | 5/1967 | Burke | |
| 3,340,671 A | 9/1967 | Loo | |
| 3,390,677 A | 7/1968 | Razimbaud | |
| 3,448,740 A | 6/1969 | Figge | |
| 3,542,240 A | 11/1970 | Solowey | |
| 3,783,895 A | 1/1974 | Weichselbaum | |
| 3,788,320 A | 1/1974 | Dye | |
| 3,822,700 A | 7/1974 | Pennington | |
| 3,938,520 A | 2/1976 | Scislowicz et al. | |
| 3,976,073 A | 8/1976 | Quick et al. | |
| 4,096,860 A | 6/1978 | McLaughlin | |
| 4,296,786 A | 10/1981 | Brignola | |
| D270,568 S | 9/1983 | Armstrong | |
| 4,490,139 A | 12/1984 | Huizenga et al. | |
| 4,516,967 A | 5/1985 | Kopfer | |
| 4,564,054 A | 1/1986 | Gustavsson | |
| 4,573,967 A | 3/1986 | Hargrove et al. | |
| 4,576,211 A * | 3/1986 | Valentini et al. | 141/329 |
| 4,581,016 A * | 4/1986 | Gettig | 604/88 |
| 4,582,223 A | 4/1986 | Kobe | |
| 4,588,403 A | 5/1986 | Weiss et al. | |
| 4,600,040 A | 7/1986 | Naslund | |
| 4,623,343 A | 11/1986 | Thompson | |
| 4,629,455 A | 12/1986 | Kanno | |
| 4,632,673 A | 12/1986 | Tiitola et al. | |
| 4,636,204 A | 1/1987 | Christopherson et al. | |
| 4,673,400 A | 6/1987 | Martin | |
| 4,673,404 A | 6/1987 | Gustavsson | |
| 4,737,150 A | 4/1988 | Baeumle et al. | |
| 4,752,287 A | 6/1988 | Kurtz et al. | |
| 4,759,756 A | 7/1988 | Forman et al. | |
| 4,768,568 A | 9/1988 | Fournier et al. | |
| 4,792,329 A | 12/1988 | Schreuder | |
| 4,804,015 A | 2/1989 | Albinsson | |
| 4,822,340 A | 4/1989 | Kamstra | |
| 4,826,492 A | 5/1989 | Magasi | |
| 4,834,717 A * | 5/1989 | Haber et al. | 604/193 |
| 4,842,585 A | 6/1989 | Witt | |
| 4,850,978 A | 7/1989 | Dudar et al. | |
| 4,864,717 A | 9/1989 | Baus, Jr. | |
| 4,872,494 A | 10/1989 | Coccia | |
| 4,878,897 A | 11/1989 | Katzin | |
| 4,889,529 A | 12/1989 | Haindl | |
| 4,898,209 A | 2/1990 | Zbed | |
| 4,909,290 A | 3/1990 | Coccia | |
| 4,932,937 A | 6/1990 | Gustavsson et al. | |
| 4,944,736 A | 7/1990 | Holtz | |
| 4,964,855 A | 10/1990 | Todd et al. | |
| 4,982,769 A | 1/1991 | Fournier et al. | |
| 4,994,048 A | 2/1991 | Metzger | |
| 4,997,083 A | 3/1991 | Loretti et al. | |
| 5,017,186 A | 5/1991 | Arnold | |
| 5,041,105 A | 8/1991 | D'Alo et al. | |
| 5,061,264 A | 10/1991 | Scarrow | |
| 5,071,413 A | 12/1991 | Utterberg | |
| 5,122,116 A * | 6/1992 | Kriesel et al. | 604/89 |
| 5,122,123 A | 6/1992 | Vaillancourt | |
| 5,137,524 A | 8/1992 | Lynn et al. | |
| 5,158,554 A | 10/1992 | Jepson et al. | |
| 5,176,673 A | 1/1993 | Marrucchi | |
| 5,199,947 A | 4/1993 | Lopez et al. | |
| 5,201,725 A | 4/1993 | Kling | |
| 5,207,658 A | 5/1993 | Rosen et al. | |
| 5,232,109 A | 8/1993 | Tirrell et al. | |
| 5,254,097 A | 10/1993 | Schock et al. | |
| 5,279,576 A | 1/1994 | Loo et al. | |
| 5,279,583 A | 1/1994 | Shober, Jr. et al. | |
| 5,279,605 A | 1/1994 | Karrasch et al. | |
| 5,308,347 A | 5/1994 | Sunago et al. | |
| 5,312,366 A | 5/1994 | Vaillancourt | |
| 5,328,480 A | 7/1994 | Melker et al. | |
| 5,334,163 A | 8/1994 | Sinnett | |
| 5,356,406 A | 10/1994 | Schraga | |
| 5,385,545 A * | 1/1995 | Kriesel et al. | 604/82 |
| 5,385,547 A | 1/1995 | Wong et al. | |
| 5,389,085 A * | 2/1995 | D'Alessio et al. | 604/198 |
| 5,405,326 A * | 4/1995 | Haber et al. | 604/110 |
| 5,445,630 A | 8/1995 | Richmond | |
| 5,447,501 A | 9/1995 | Karlsson et al. | |
| 5,456,675 A | 10/1995 | Wolbring et al. | |
| 5,470,522 A | 11/1995 | Thome et al. | |
| 5,478,328 A | 12/1995 | Silverman et al. | |
| 5,478,337 A | 12/1995 | Okamoto et al. | |
| 5,492,531 A | 2/1996 | Post et al. | |
| 5,514,117 A | 5/1996 | Lynn | |
| 5,515,871 A | 5/1996 | Bittner et al. | |
| 5,536,259 A | 7/1996 | Utterberg | |
| 5,575,780 A | 11/1996 | Saito | |
| 5,593,028 A | 1/1997 | Haber et al. | |
| 5,613,954 A | 3/1997 | Nelson et al. | |
| 5,632,735 A | 5/1997 | Wyatt et al. | |
| 5,647,845 A | 7/1997 | Haber et al. | |
| 5,685,866 A | 11/1997 | Lopez | |
| 5,752,942 A | 5/1998 | Doyle et al. | |
| 5,766,147 A | 6/1998 | Sancoff et al. | |
| 5,766,211 A | 6/1998 | Wood et al. | |
| 5,782,872 A | 7/1998 | Muller | |
| 5,795,336 A * | 8/1998 | Romano et al. | 604/192 |
| 5,817,083 A | 10/1998 | Shemesh et al. | |
| 5,820,609 A | 10/1998 | Saito | |
| 5,827,262 A | 10/1998 | Neftel et al. | |
| 5,837,262 A | 11/1998 | Golubev et al. | |
| 5,875,931 A | 3/1999 | Py | |
| 5,879,345 A * | 3/1999 | Aneas | 604/411 |
| 5,897,526 A | 4/1999 | Vaillancourt | |
| 5,934,510 A | 8/1999 | Anderson | |
| 5,984,899 A * | 11/1999 | D'Alessio et al. | 604/198 |
| 6,022,339 A | 2/2000 | Fowles et al. | |
| 6,063,068 A | 5/2000 | Fowles et al. | |
| D427,308 S | 6/2000 | Zinger | |
| 6,070,623 A * | 6/2000 | Aneas | 141/329 |
| 6,071,270 A | 6/2000 | Fowles et al. | |
| 6,090,091 A | 7/2000 | Fowles et al. | |
| 6,113,068 A | 9/2000 | Ryan | |
| 6,113,583 A | 9/2000 | Fowles et al. | |
| 6,142,446 A | 11/2000 | Leinsing | |
| 6,146,362 A | 11/2000 | Turnbull et al. | |
| 6,209,738 B1 * | 4/2001 | Jansen et al. | 215/247 |
| 6,221,065 B1 | 4/2001 | Davis | |
| 6,245,056 B1 | 6/2001 | Walker et al. | |
| D445,501 S | 7/2001 | Niedospial, Jr. | |
| 6,253,804 B1 | 7/2001 | Safabash | |
| 6,258,078 B1 * | 7/2001 | Thilly | 604/411 |
| 6,387,074 B1 * | 5/2002 | Horppu et al. | 604/89 |
| 6,453,956 B2 | 9/2002 | Safabash | |
| 6,471,674 B1 | 10/2002 | Emig et al. | |
| 6,517,523 B1 | 2/2003 | Kaneko et al. | |
| 6,537,263 B1 | 3/2003 | Aneas | |
| 6,571,837 B2 * | 6/2003 | Jansen et al. | 141/329 |
| 6,591,876 B2 | 7/2003 | Safabash | |
| 6,644,367 B1 * | 11/2003 | Savage et al. | 141/383 |
| 6,685,692 B2 | 2/2004 | Fathallah | |
| 6,715,520 B2 | 4/2004 | Andreasson et al. | |
| 6,761,286 B2 | 7/2004 | Py et al. | |
| D495,416 S | 8/2004 | Dimeo et al. | |
| 6,786,244 B1 * | 9/2004 | Jones | 141/2 |
| D506,256 S | 6/2005 | Miyoshi et al. | |
| 6,960,194 B2 | 11/2005 | Hommann et al. | |
| 7,000,806 B2 | 2/2006 | Py et al. | |
| 7,080,672 B2 | 7/2006 | Fournier et al. | |
| 7,297,140 B2 | 11/2007 | Orlu et al. | |
| D570,477 S | 6/2008 | Gallogly et al. | |
| D572,820 S | 7/2008 | Gallogly et al. | |
| D577,438 S | 9/2008 | Gallogly et al. | |
| D577,822 S | 9/2008 | Gallogly et al. | |
| D582,033 S | 12/2008 | Baxter et al. | |
| D605,755 S | 12/2009 | Baxter et al. | |
| 7,703,486 B2 | 4/2010 | Costanzo | |
| D616,984 S | 6/2010 | Gilboa | |
| 7,744,581 B2 | 6/2010 | Wallen et al. | |
| 2001/0021825 A1 | 9/2001 | Becker et al. | |
| 2001/0025671 A1 | 10/2001 | Safabash | |
| 2002/0002352 A1 | 1/2002 | Becker et al. | |

| | | |
|---|---|---|
| 2002/0082586 A1 | 6/2002 | Finley et al. |
| 2002/0127150 A1 | 9/2002 | Sasso |
| 2002/0177819 A1* | 11/2002 | Barker et al. ............... 604/232 |
| 2003/0010717 A1 | 1/2003 | Brugger et al. |
| 2003/0070726 A1 | 4/2003 | Andreasson et al. |
| 2003/0106610 A1* | 6/2003 | Roos et al. ................. 141/346 |
| 2003/0107628 A1 | 6/2003 | Fowles et al. |
| 2003/0199846 A1* | 10/2003 | Fowles et al. ............... 604/403 |
| 2003/0233083 A1 | 12/2003 | Houwaert et al. |
| 2004/0116858 A1 | 6/2004 | Heinz et al. |
| 2004/0199139 A1* | 10/2004 | Fowles et al. ............... 604/414 |
| 2004/0215147 A1 | 10/2004 | Wessman et al. |
| 2005/0215977 A1 | 9/2005 | Uschold |
| 2006/0025747 A1* | 2/2006 | Sullivan et al. .............. 604/411 |
| 2006/0106360 A1 | 5/2006 | Wong |
| 2006/0111667 A1 | 5/2006 | Matsurra et al. |
| 2006/0157984 A1 | 7/2006 | Rome et al. |
| 2006/0186045 A1 | 8/2006 | Jensen et al. |
| 2007/0021725 A1 | 1/2007 | Villette |
| 2007/0060841 A1 | 3/2007 | Henshaw |
| 2007/0088313 A1 | 4/2007 | Zinger et al. |
| 2007/0106244 A1 | 5/2007 | Mosler et al. |
| 2007/0179441 A1 | 8/2007 | Chevallier |
| 2007/0270759 A1 | 11/2007 | Pessin |
| 2007/0270778 A9 | 11/2007 | Zinger et al. |
| 2008/0045919 A1 | 2/2008 | Jakob et al. |
| 2008/0103453 A1 | 5/2008 | Liversidge |
| 2008/0103485 A1 | 5/2008 | Kruger |
| 2008/0172039 A1 | 7/2008 | Raines |
| 2008/0223484 A1 | 9/2008 | Horppu |
| 2008/0287920 A1 | 11/2008 | Fangrow et al. |
| 2008/0312634 A1 | 12/2008 | Helmerson et al. |
| 2009/0254042 A1 | 10/2009 | Gratwohl et al. |
| 2010/0137827 A1 | 6/2010 | Warren et al. |
| 2010/0204671 A1 | 8/2010 | Kraushaar et al. |
| 2010/0243099 A1 | 9/2010 | Yodfat |

FOREIGN PATENT DOCUMENTS

| | | |
|---|---|---|
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0453264 | 10/1991 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 288664 | 7/1990 |
| JP | 04-227275 | 8/1992 |
| JP | 3030963 | 8/1996 |
| JP | 11-009656 | 1/1999 |
| JP | 2000167022 | 6/2000 |
| JP | 2001505092 | 4/2001 |
| JP | 2001-161792 | 6/2001 |
| JP | 2001293085 | 10/2001 |
| JP | 2002524217 | 8/2002 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2005/074860 | 8/2005 |
| WO | WO 2006/082350 | 8/2006 |
| WO | WO 2006/083333 | 8/2006 |
| WO | WO 2008/115102 | 9/2008 |
| WO | WO 2006/138184 | 12/2009 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009. (2 pages).

* cited by examiner

PIERCING MEMBER PROTECTION DEVICE

TECHNICAL FIELD

The present invention concerns a female piercing member protection device for connection with a male connection part, a male connection part, and a method for connecting the female piercing member protection device with the male connection part.

BACKGROUND OF THE INVENTION

Administration of hazardous medicaments such as cytotoxins and the like, has long been a nuisance to the personal which on daily basis administrate the hazardous medicaments. During preparation of medicaments, administration or after treatment, nursing personal is exposed to the risk of contamination from the hazardous medicaments. Such contamination may be in the form of liquid medicaments, derived from spillage due to ill handling or just wrong handling of equipments or instruments. Leakage from technical equipment which has been used right is however also a problem, even if leakage occur in very small doses. Due to long exposure to hazardous medicaments nursing personal can still be ill from very small quantities of hazardous medicaments. It is therefore important to minimize leakage and minimize the risk of leakage.

One specific hazardous step is when e.g. nursing personal is transferring a medicament from one fluid container to another; such transfer usually involves the use of a piercing member such as a needle. To protect the nursing personal involved, piercing member protection devices are commonly used. Such devices are arranged to protect the user, not only from contamination but also from accidentally piercing themselves or any other third persons.

In the patent publication of U.S. Pat. No. 6,890,328 a connector device for establishing fluid communication between a diluents container having side walls and a drug vial is described. The drug vial may be selectively attached to the device without piercing the closure of the vial and without breaching the hermetic seal of the fluid accessing portions of the piercing member. Means are provided for connecting the vial receiving chamber to the liquid container. The device is movable from an inactivated position, where the piercing member is outside the sidewalls and no fluid flows between the liquid container and the drug vial, to an activated position, where fluid flows through the fluid pathway between the liquid container and the drug vial. The device is movable from the inactivated position to the activated position by a force applied to the device outside the liquid container. However at any time the drug vial and diluents container can be disconnected, leaving the needle exposed to the nursing personal. The needle at such stage is full of hazardous medicaments.

Another medical connector is described in U.S. Pat. No. 5,514,117, for connecting transferring a fluid from a first fluid container to a second fluid container for administration of fluid to a patient. The medical connector is formed of two components. The first component includes a cannula hub to which a cannula is mounted, a base extending from the hub and fingers extending from the base. The second component is a collar including a support and bars extending therefrom. The collar is manually slideable along the first component in the direction the cannula extends between a retracted position and a locking position. The bars engage the fingers to flex into engagement with a junction terminal. The bars are elastically deformable to provide a spring force for locking the fingers on the junction terminal. The medical connector have however the drawback that the locking of the fingers easily can be unlocked by simply pulling apart either the collar or the junction terminal and thereby expose a user for contaminants.

SUMMARY OF THE INVENTION

It is an object of the present invention to at least partly solve the above mentioned problems. More particularly, the mentioned problems are at least partly solved by a female piercing member protection device, having a longitudinal axis A, for connection with a male connection part. The female piercing member protection device comprises; an outer casing having a first and a second end and an inner and an outer side, a connection member having a first and a second end. The connection member is arranged to, and at least partly enclosed in, the outer casing. Further is the outer casing arranged to be moved between a first and a second position, wherein when the outer casing is in its first position, the connection member is substantially locked from movement along the longitudinal axis A, and when the outer casing is in its second position the connection member is able to move along the longitudinal axis A. The female piercing member protection device additionally comprises an activated position and an inactivated position. The connection member is arranged to connect to the male connection part by means of a deformable locking device, wherein when the outer casing is in the second position, the deformable locking device is prevented from deformation by the outer casing so as to prevent disengagement of the male connection part.

The present invention provides for a secure piercing protection device which permits a fluid container to be connected to the piercing device, secured and thereafter activated so as to permit for a fluid communication to be established. The deformable locking device provides for an easy connection, which actually permits a user to, after connection to the piercing device, let go of the fluid container. The piercing member protection device can thereafter substantially lock the connected fluid container so that accidental disconnection is effectively prevented. Only after the piercing member device has been locked to the fluid container, via the male connection part, is it possible to move it to its activated position, hence, a very safe drug or medicament administration and transfer can be achieved with this device, since the needle is never exposed. Further no orientation of the male connection part is needed before connection; this enables a fast and simple connection.

For additional safety, the connection member is preferably arranged between the first and second end of the outer casing. The outer casing will then function as a protective sleeve, covering the interface between the piercing member protection device and the connected fluid container.

In one embodiment of the present invention, the deformable locking device comprises at least one deformable locking flange, which may or may not form an integrated part of the connection member. It is from a manufacturing point of view however easier to manufacture the deformable locking flange as an integrated part, i.e. in one piece. The connection member may be equipped with at least two, at least three or at least four deformable locking flanges. Alternatively, a plurality of 5 to 15 deformable locking flanges may be present.

The outer casing may comprise at least one aperture, which when the connection member is in the first position, the at least one aperture and the at least one deformable locking flange is substantially aligned, so that the deformable locking flange can deform into the aperture during connection with the male connector. When the outer casing is in the second position, the deformable locking flange is displaced from the aperture in the outer casing, so that the deformable locking flange is substantially unable to disengage from the male connector. Alternatively, the aperture may be replaced with a cavity arranged on the inner side of the outer casing. A combination of apertures and cavities are of course also possible. Cavities may be preferred since the outer casing will protect the deformable locking flanges, however, apertures permits a user to more readily watch and control the connection which is established. The number of apertures, cavities, or apertures and cavities should preferably, although not necessarily, be equal to the number of locking flanges, e.g. two locking flanges can easily be in working cooperation with one aperture or one cavity which can embrace them both.

In an embodiment of the present invention, the female piercing member protection device comprises a second locking device, which can substantially lock the connection member from movement along the longitudinal axis A, when the connection member is in the activated position. The second locking device enables a user to safely let go of the piercing device without fear or risk of a disengagement of the piercing member after fluid communication has been established. Preferably, the second locking device comprises a locked position in which the connection member is substantially unable to slide along the longitudinal axis A, and an unlocked position in which the connection member is substantially able to slide along the longitudinal axis A. The second locking device may be in the form of a turnable locking ring which encompasses the outer casing. The turnable ring is preferably provided with a locking protrusion which is in working cooperation with the outer casing, and a channel arranged in the outer casing, as will be described below.

The connection member comprises at least one barrier member, preferably two barrier members. The two barrier members may be arranged substantially parallel with respect each other and so as to intersect the longitudinal axis A. Additionally they may be arranged so as to form a piercing tip protection chamber between the two barrier members. The barrier members provide for a leakage safe arrangement, both during fluid transfer and after fluid transfer, at which medicament residuals may be present inside the protection device.

The present invention also concerns a method for connecting a female piercing member protection device with a male connection part. The female piercing member protection device having a longitudinal axis (A), an outer casing and a connection member arranged inside the outer casing, the method comprising the steps of:

Connecting the connection member to the male connection by means of a deformable locking device and moving the outer casing with respect to the connection member from a first position, in which the female piercing member protection device is in an inactivated state and in which the connection member is substantially unable to slide along the longitudinal axis A, to a second position, in which the female piercing member protection device is in an inactivated state and in which the connection member is substantially able to slide along the longitudinal axis A. Further, when the outer casing is in the second position, the fluid container is substantially unable to disengage from the piercing member protection device.

The method according to the present invention provides for a safe connection between the male connection part and the female piercing member protection device. The female piercing member protection device may thereafter be activated by moving the connection member to the activated position and thereafter be substantially locked in the activated position by means of a locking ring arranged around the outer casing.

The present invention also concerns a male connection part for connection with the female piercing member protection device. The male connection part comprises a longitudinal cylinder like body having a longitudinal axis C, a first and a second side, an outer and an inner surface. A barrier member is arranged at the centre of the first side of the male connection member, intersecting the longitudinal axis C. Further is a fluid communication channel formed by the inner surface, said fluid communication channel extends from the barrier member of the male connection part to the second side of the male connection part. The male connection part further comprises at least one turning grip protrusion to provide for an increased turning friction between the female piercing member protection device, after assembly. The male connection part provides for a safe connection, in terms of leakage protection, with the female piercing member connection device. Further may a circumferential wall surround the first end of the male connection part. The wall permits a rigid coupling while, at the same time, prevent direct exposure of the barrier member to e.g. improper handling.

To increase the turning friction, at least one turning grip protrusion is arranged on said circumferential wall. This will permit the male connection part to be inserted only a moderate distance into the female piercing member protection device, while still give the above mentioned advantages of the circumferential wall. In fact, the at least one turning grip protrusion will stiffen the circumferential wall even more, and thereby provide for a rigid and secure connection. The male connection part may comprise between 1-20 turning grip protrusions, one preferred embodiment comprises three turning grip protrusions. The at least one turning grip protrusion runs substantially parallel with said longitudinal axis C, this may e.g. provide additional rigidity to the circumferential wall of the male connection part.

BRIEF DESCRIPTION OF THE DRAWINGS

The present invention will hereafter be described in greater detail with reference to the accompanying drawing wherein.

DETAILED DESCRIPTION OF PREFERRED EMBODIMENTS

Figure 1:
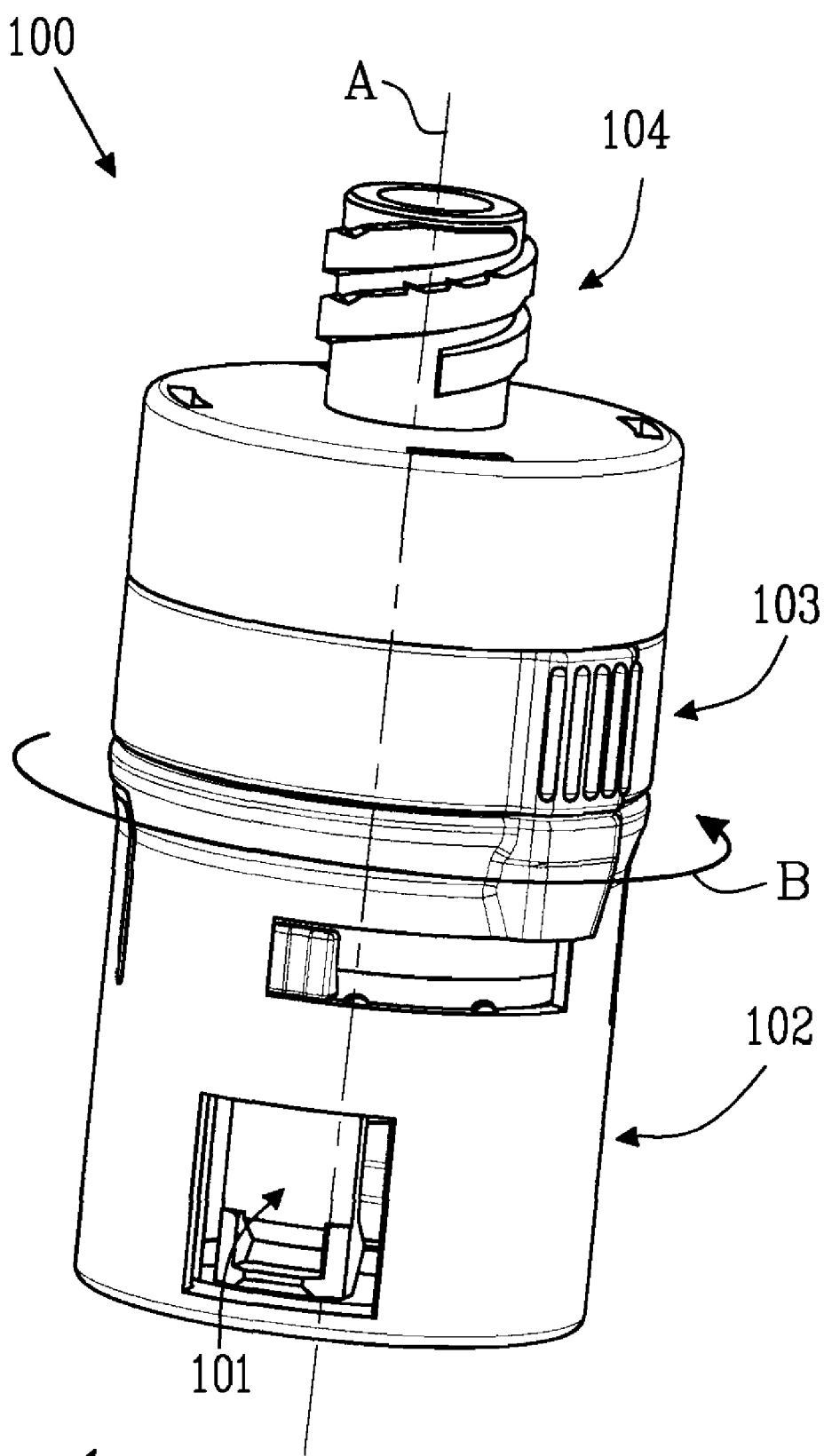
FIG. 1 show the female piercing member protection device according to the present invention in perspective.

In the following section different embodiments according to the present invention will be described in greater detail. FIG. 1a shows a female piercing member protection device 100 having a longitudinal axis A and a transverse axis B, for providing a fluid communication between a first and a second fluid container. The female piercing member protection device 100 comprises a connection member 101 to connect to the first fluid container via a male connection part. The connection member 101 is at least partly enclosed by a turnable outer casing 102, which can be turned between a first and a second position. The first position in which the connection member 101 is substantially unable to slide along the longitudinal axis A, and a second position in which the connection member 101 is it substantially able to slide along the longitudinal axis A. The first position is an inactivated position in which the female piercing member protection device 100 fully protects the piercing member from exposure and at the same time is protected in terms of that the connection member 101 is substantially unable to slide to an activated position. The female piercing member protection device 100 also comprises an activated position in which the piercing member is exposed so as to provide for a fluid communication between the first and the second fluid container. The activated position can only be reached when the outer casing 102 has been turned to the second position, and the connection member 101 is moved along the longitudinal axis A to the activated position.

The outer casing 102 is arranged to cover the connection member 101 so as to provide for a protective sleeve, in which the connection member may slide. A locking ring 103 is arranged around the periphery of the outer casing and function as a second locking device which can substantially prevent the connection member from sliding between the activated and inactivated position by means of being turned between a locked position and an unlocked position. Connection means 104 is arranged opposite the connection member 102 to the outer casing 102 so as to allow for the connection to the second fluid container. A piercing member (not shown) is arranged to the connection means 104 so as to provide for fluid communication between a first and a second fluid container.

Figure 2:
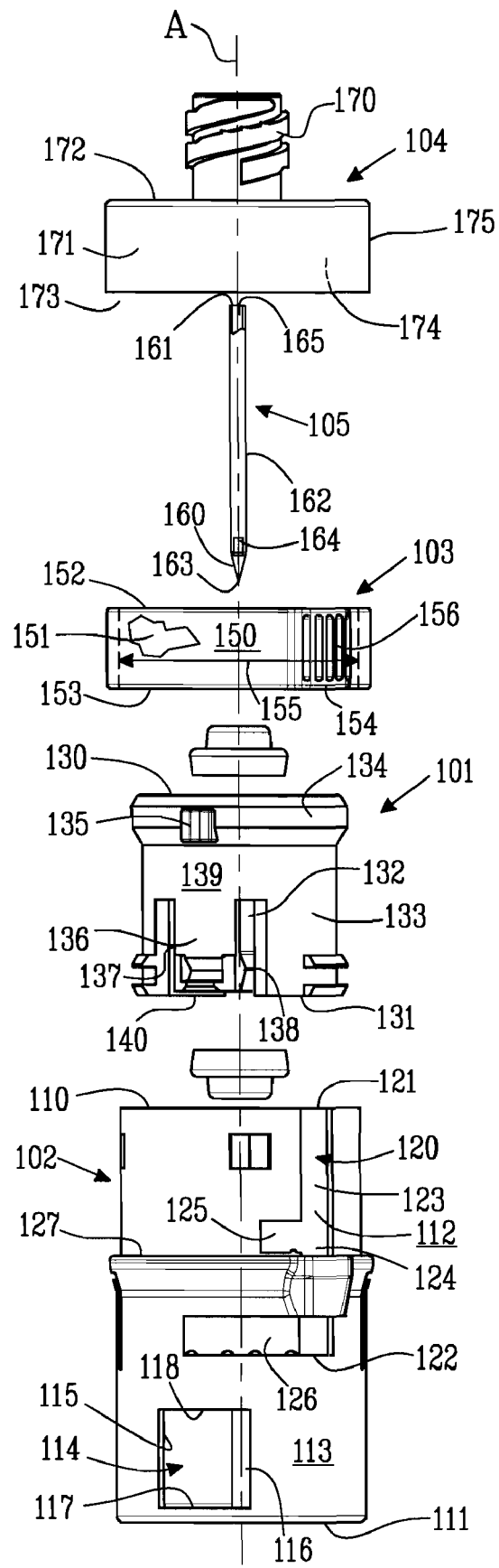
FIG. 2 shows an exploded view of the female piercing member protection device shown in FIG. 1.

In FIG. 2, each component is shown in an exploded view along the longitudinal axis A, and will be described in greater detail below.

Turning first to the outer casing 102, the outer casing 102 comprises a first and a second side 110, 111, an inner and an outer side 112, 113 and have substantially the form of a hollow cylinder. At least one aperture 114 is arranged in the proximity of the second end 111 of the outer casing 102. The aperture 114 is substantially rectangular with a first and a second longitudinal side 115, 116 and a first and a second transverse side 117, 118.

The aperture 114 is intended to be assembled in working cooperation with a locking flange arranged on the connection member 101.

A straight channel 120 having a first and a second end 121, 122 is arranged in the outer casing 102, extending trough the outer casing 102. The straight channel 120 further extends from the first side 110 of the outer casing towards the second end 111 of the outer casing 102 and passes the middle of the outer casing 102, with respect to the longitudinal axis A of the outer casing 102. The straight channel 120 stops just above the aperture 114, with respect to the longitudinal axis A. The straight channel 120 comprises an assembly part 123 and a working part 124. The assembly part 123 and the working part 124 are separated by a connection member locking channel 125 which extends substantially perpendicular from the middle of the straight channel 120, along the outer casing 102. Additionally, an activation and inactivation positioning channel 126 extends substantially perpendicular along the outer casing 102, from the second end 122 of the straight channel 120. The connection member locking channel 125 extends slightly shorter along the outer casing 102 than the positioning channel 126. Altogether, the straight channel 120, the connection member locking channel 125 and the positioning channel 126 substantially form an F-shaped channel system. The outer casing can preferably be turned 5-180°, more preferably 20-120°, most preferred 40-95°, between the first and second position.

A stop flange 127 is arranged between the connection member locking channel 125 and the positioning channel 126. The stop flange 127 extends around the periphery of the outer casing 102 and crosses the working part 124 of the straight channel 120. After the outer casing 102 has been assembled with the connection member 101, a locking ring 103 is placed adjacent the stop flange 127 and around the periphery of the outer casing 102. The stop flange 127 prevents the locking ring 103 from sliding along the longitudinal axis A in a direction towards the second side 111 of the outer casing 102.

Further shown in FIG. 2 is the connection member 101. The connection member 101 comprises a substantially hollow cylinder sleeve which has an outer diameter slightly less than the inner diameter of the outer casing. During assembly with the outer casing 102, the connection member 101 is inserted into the outer casing from the first side 110 of the outer casing 102. The connection member 101 comprises a first and a second side 130, 131 and an inner and an outer side 132, 133. A circumferential flange 134 extends around the periphery of the connection member 101 at the first side 130 of the connection member 101. A protrusion 135 protrudes out from the periphery of the circumferential flange 134 of the connection member 101. The protrusion 135 is during assembly intended to slide into the assembly part 123 of the straight channel 120 and to operate in the connection member locking channel 125 and the positioning channel 126 as well as the working part 124, during use of the female piercing member protection device 100.

At least one deformable locking flange 136 is arranged substantially parallel with the longitudinal axis A. The deformable locking flange 136 comprises a first and a second longitudinal side 137, 138 and a first and a second transverse side 139, 140. The first transverse side 139, which is an integrated part of the connection member 101, is arranged in the proximity of the middle of the connection member 101, with respect to the longitudinal axis A. Hence the deformable locking flange 136 is an integrated part of the connection member 102. The deformable locking flange 136 extends from the middle of the connection member 101 to the second side 131 of the connection member 101. Small channels separate, and form, the first and the second longitudinal side 137, 138 from the connection member 101. After assembly, the deformable locking flange 136 of the connection member 101 is intended to be in working cooperation with the aperture 114 of the outer casing 102, and to lock onto a male connection member, as will be described below.

The aperture 114 of the outer casing and the deformable locking flange 136 of the connection member 101 has been described in singular; however, in a preferred embodiment of the present invention, the outer casing comprises at least two opposing apertures 114 and at least two opposing deformable locking flanges 136.

The locking ring 103 is in the form of a ring-like sleeve member comprising an outer and an inner surface 150, 151 and a first and a second transverse side 152, 153. A locking protrusion 154 (shown in FIGS. 3 to 7) protrudes between the first and the second side 152, 153 from the inner surface 151 of the locking ring 103. The locking ring comprises an inner diameter 155 which is large enough for the locking ring 103 to snugly fit around the outer casing 102 after assembly. The distance between the first and the second side 152, 153 of the locking ring 103 is substantially smaller than the length of the inner diameter 155 providing the substantially ring-like form to the locking ring 103. The outer surface 150 of the locking ring 103 comprises at least one grip protrusion 156 which extends out from wall of the locking ring 103. Preferably is a plurality of grip protrusions arranged on the locking ring 103. Such a grip protrusion aids a user during turning of the locking ring 103. Alternatively, the grip protrusion is replaced with a see-through opening which would in the shown embodiment of the present invention be aligned with the protrusion 154 and run substantially parallel with the protrusion 154. Such see-through opening can be covered with a protective window if necessary. The purpose of the see through opening 156 is for a user to have an indication of whether the locking ring 103 is in the locked or unlocked position. As an alternative to a see through opening, the locking ring 103 can be manufactured from a transparent material.

A piercing member 105 in the form of a hollow needle comprises a first and a second end 160, 161 and an envelope surface 162. The first end 160 comprises a piercing tip 163 intended to pierce a male connector of a fluid container during use. A fluid outlet opening 164 is arranged in the proximity of the piercing tip 163, a fluid inlet opening 165 is arranged at the second end 161. Although the terms outlet and inlet openings are used, the openings and the piercing member 105 are not restricted to a one way flow.

The connection means 104 comprises a threaded portion 170 extending along the longitudinal axis A and arranged so that a fluid container can be attached to the connection means 104. The threaded portion 170 comprises an opening (not shown) into which the second end 161 of the piercing member 105 can be arranged so that the fluid inlet opening 165 is in fluid communication with a fluid container after connection. The threaded portion 170 is in the shown embodiment a conventional luer-lock arrangement. A sleeve member 171 is arranged to the threaded portion 170. The sleeve member 171 comprises a first and a second transverse side 172, 173 extending substantially transverse to the longitudinal axis A, an outer and an inner surface 174, 175. The threaded portion is arranged substantially in the centre of the first transverse side 172 of the sleeve member 171 which comprises a larger diameter than the threaded portion 170. The sleeve member 171 is further arranged with an assembly opening (not shown) at the second end 173 of the sleeve portion. The assembly opening extends substantially from the second transverse side 173 to the proximity of the first transverse side 172 of the sleeve member 171. After assembly, the assembly opening is intended to partly encompass at least the first side 110 of the outer casing 102.

Additionally in FIG. 2 is a first and a second barrier member shown; which will be described in greater detail below.

Figure 3:
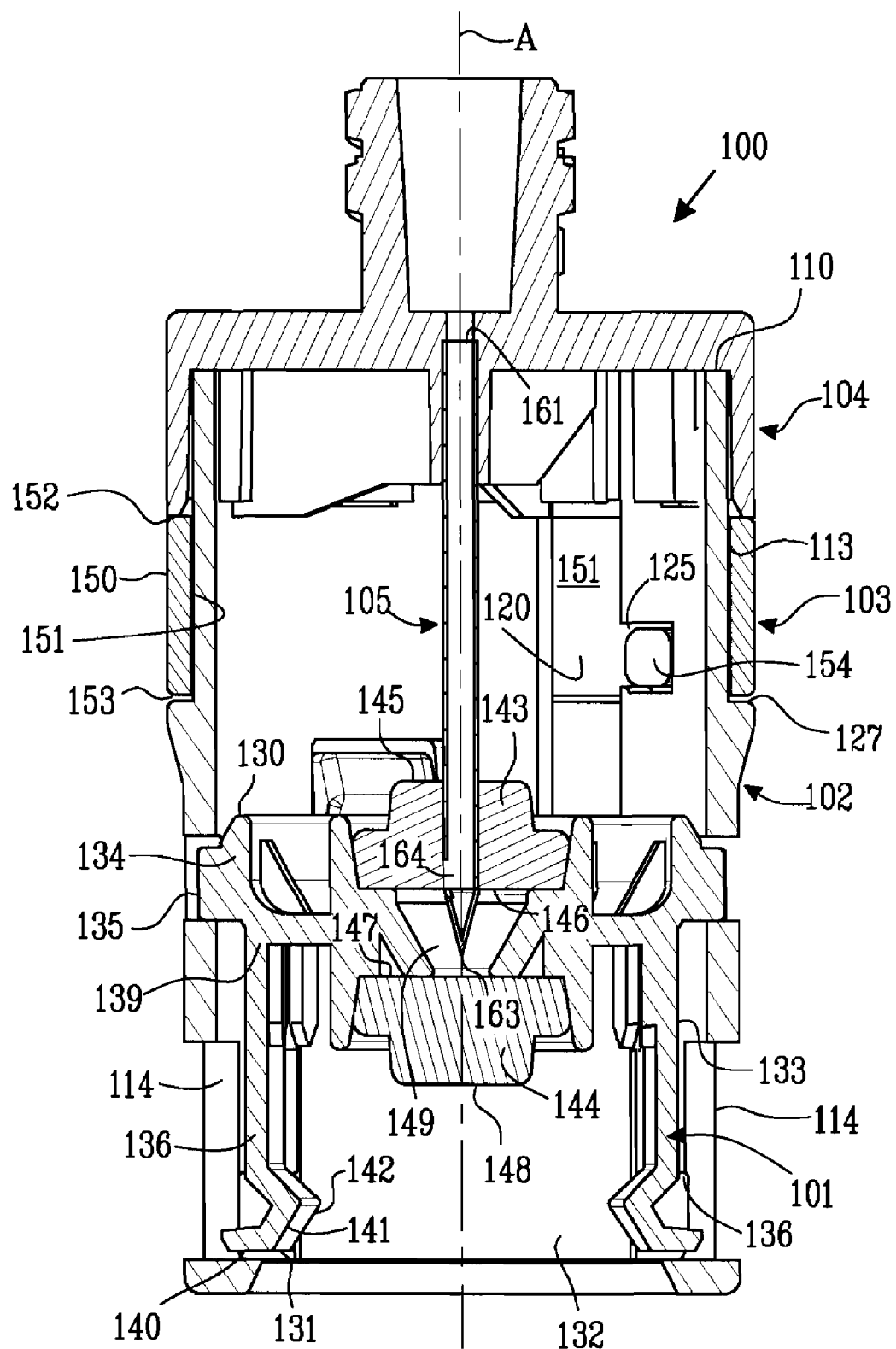
FIG. 3 shows a cross section of the female piercing member protection device shown in FIG. 1.

FIG. 3 shows a cross section of the earlier described embodiment of the present invention after assembly. More specifically FIG. 3 shows the female piercing member protection device 100 with a longitudinal axis A, and comprising a connection member 101, an outer casing 102 arranged to cover the connection member 101 so as to provide for a protective sleeve. A locking ring 103 is arranged around the periphery of the outer casing 102 and function as a second locking device which can substantially prevent the connection member from sliding between an activated and an inactivated position along the longitudinal axis A. Connection means 104 is arranged to the outer casing 102 so as to permit for the connection to the second fluid container. A piercing member 105 is arranged to the connection means 104 so as to provide for fluid communication between a first and a second fluid container during use.

The connection member 101 comprises as described above a first and a second side 130, 131 and an inner and an outer side 132, 133. A circumferential flange 134 extends around the periphery of the connection member 101 at the first side 130 of the connection member 101. A protrusion 135 protrudes out from the periphery of the circumferential flange 134 of the connection member 101.

The locking flange 136 which is arranged substantially parallel with the longitudinal axis A, comprises, as mentioned, a first and a second transverse side 139, 140. In the proximity of the second transverse side 140 of the locking flange 136, the locking flange 136 comprises a hook like configuration, in the shown embodiment, the hook like configuration comprises a fold portion 141 which together with the locking flange 136 provide a snap-on connection to a male connection part. The second transverse side 140 of the locking flange comprises a substantially transverse portion, with respect to the longitudinal axis A, which continues with an angle towards the longitudinal axis A to a folding tip 142, and then continues away from the longitudinal axis A, back to run substantially parallel with the longitudinal axis A. As mentioned, the folding tip 142 points towards the longitudinal axis A.

The locking flange 136 of the connection member 101 is as mentioned in working cooperation with the aperture 114 of the outer casing 102. As can be seen in FIG. 3, the connection member comprises two locking flanges 136 which are arranged to be in working cooperation with two apertures 114 on the outer casing 102. This working cooperation will be described in greater detail with reference to FIG. 5 below.

The connection member 101 is further arranged with a first and a second barrier member 143, 144 arranged so as to intersect the longitudinal axis A. The first and the second barrier member 143, 144 each has a substantially disc shaped form and respectively comprises a first and a second transverse side 145, 146, 147, 148. While being arranged substantially parallel with respect to each other, the space between the second transverse side 146 of the first barrier member 143 and the first transverse side 147 of the second barrier member 144 form a piercing tip protection chamber 149. As is shown in FIG. 3, the second end 161 of the piercing member is attached to the connection means 104, permitting the piercing member 105 to extend aligned with the longitudinal axis A, and partly through the first barrier member 143, to the piercing tip protection chamber 149. The piercing tip 163 of the piercing member 105 is arranged in the piercing tip protection chamber 149. The outlet opening 164 of the piercing member 105 is positioned at least partly inside the first barrier member 143 so as to provide for a protective lid to the outlet opening 164 of the piercing member 105. The piercing tip 163 may however be positioned fully inside the first barrier member 143, or fully inside the piercing tip protection chamber 149.

The first and second barrier members 143, 144 has been described as two separate barrier members, however, the two separate barrier member can be replaced with one barrier member comprising a piercing tip protection chamber, or with a barrier member without a piercing tip protection chamber.

In one embodiment, a piercing member protection device comprises a piercing member, wherein said piercing member comprises a fluid opening in the proximity of a piercing tip, at least one barrier member is arranged to the piercing member protection device wherein the fluid opening of the piercing member is fully enclosed in the barrier member, so that the barrier member provides a fluid leakage protection device for the piercing member protection device. The piercing member protection device is preferably a female piercing protection device.

The outer casing 102 can, as mentioned above, be turned between a first position and a second position, wherein when the outer casing 102 is in its first position; the male connection part can be attached with a snap-on connection to the connection member 101. In the first position the male connection member may also be released from the snap-on connection, however, such detachment needs a certain force in order to overcome the snap-on connection. When the outer casing 102 is in its second position, the locking flanges 136 of the connection member 101 are displaced from the apertures 114 of the outer casing 102, this will be described in greater detail below.

Further in FIG. 3, the locking ring 103 is arranged circumferentially around the outer surface 113 of the outer casing 102 and is positioned between the stop flange 127 of the outer casing 102 and the connection means 104. The connection means 104 is attached in the proximity of the first side 110 of the outer casing 102.

Figure 4A:
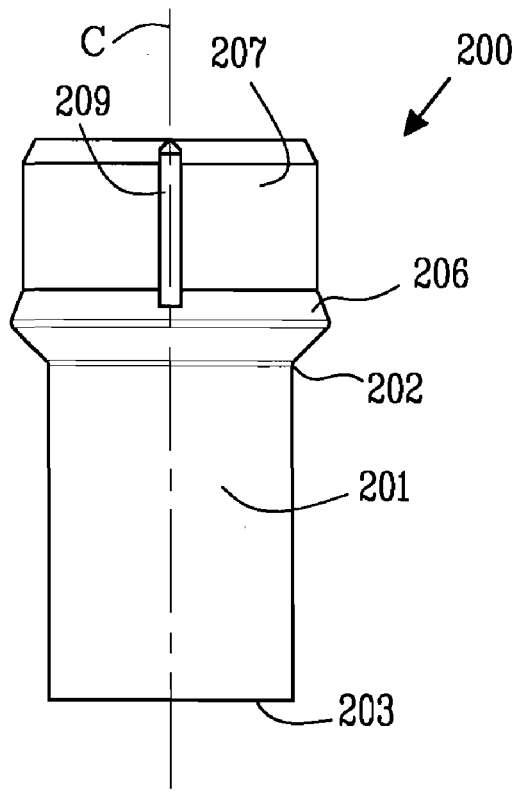
FIGS. 4a-4b shows, in perspective, a male connection part for connection with the female piercing member protection device shown in FIG. 1.
Figure 4B:
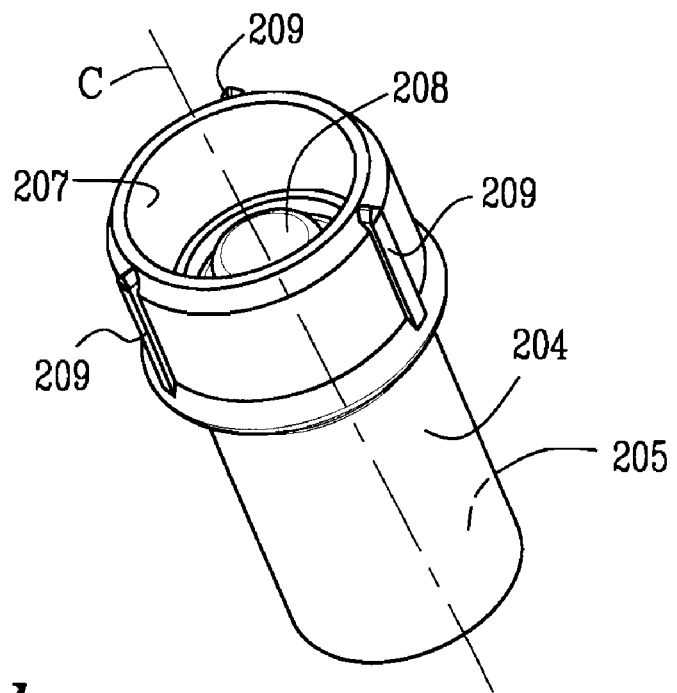

In FIGS. 4a and 4b a male connection part will be described in greater detail. The male connection part may form a permanent or a temporarily connection part on e.g. a fluid container such as an infusion bag, infusion line, or the like, e.g. by means of a luer-lock, spike device, welding means, molding or adhesive means. The male connection part 200 comprises a longitudinal cylinder like body 201 having a longitudinal axis C. The male connection part 200 further comprises a first and a second side 202, 203, an outer and an inner surface 204, 205. At the first side of 202 of the male connection part 200 is a transverse locking flange 206 arranged. The transverse locking flange 206 extends around the periphery of the outer surface 204 of the male connection part 200 and is intended to cooperate with the locking flange 136 of the connection member 101.

In the shown embodiment of the male connection part 200, a circumferential wall 207 surrounds the first end 202 of the male connection part 200, as shown in FIG. 4b. The circumferential wall 207 is arranged to at least partly encompass at least a part of the second barrier member 144 of the connection member 101 after connection, to provide for a steady and rigid connection between the parts, as well as provide a protective wall against negative handling, e.g. touching, which might lead to damages of e.g. a barrier member 208. The barrier member 208 is arranged at the centre of the first side 202 of the male connection member 200, intersecting the longitudinal axis C. The barrier member 208 of the male connection part 200 is after assembly with the female piercing member protection device 100 intended to provide for a double barrier member coupling together with the second barrier member 144 of the connection member 101. A fluid communication channel 210 (not shown), formed by the inner surface 205, extends from the barrier member 208 of the male connection part 200 to the second side 203 of the male connection part 200.

The male connection part 200 can further be arranged with at least one turning grip protrusion. In the shown embodiment, the male connection part 200 is equipped with 3 turning grip protrusions 209. The turning grip protrusions 209 are arranged on the outer surface of the circumferential wall 207, permitting the turning grip protrusions 209 to interact with the inner side 132 of the connection member 101. The tree turning grip protrusions 209 are symmetrically spread around the outer surface of the circumferential wall 207 so as to permit a good grip, and to prevent that more than one turning grip protrusions 209 will be positioned on the locking flange 136 of the connection member 101. They further run substantially along the longitudinal axis C at least along a part of the circumferential wall 207.

In those cases the male connection part 200 is arranged with turning grip protrusions, the inner side of the connection member is preferably arranged with corresponding turning grip grooves (not shown). The number of turning grip protrusions 209 on the male connection part 200 may be from 1 to 20, preferably 2-10, more preferably 3-8, generally symmetrically spread around the circumferential wall 207 or any other suitable part of the connection member 200. The number of turning grip grooves, also they generally symmetrically spread around the inner surface 132 of the connection member 101, may be from 1 to 19, preferably 1-9, more preferably 2-7. Most preferably, the number of turning grip protrusions 209 are more than the number of turning grip grooves, preferably one more. The purpose of the turning grip protrusions 209 is to prevent the connection member 101 from turning with respect to the male connection part 200 after assembly, this in turn will provide for a safe turning, with respect to the outer casing 102. The male connection part thereby provides for an increased turning friction between the female piercing member protection device, and especially the connection member, after assembly.

Figure 5:
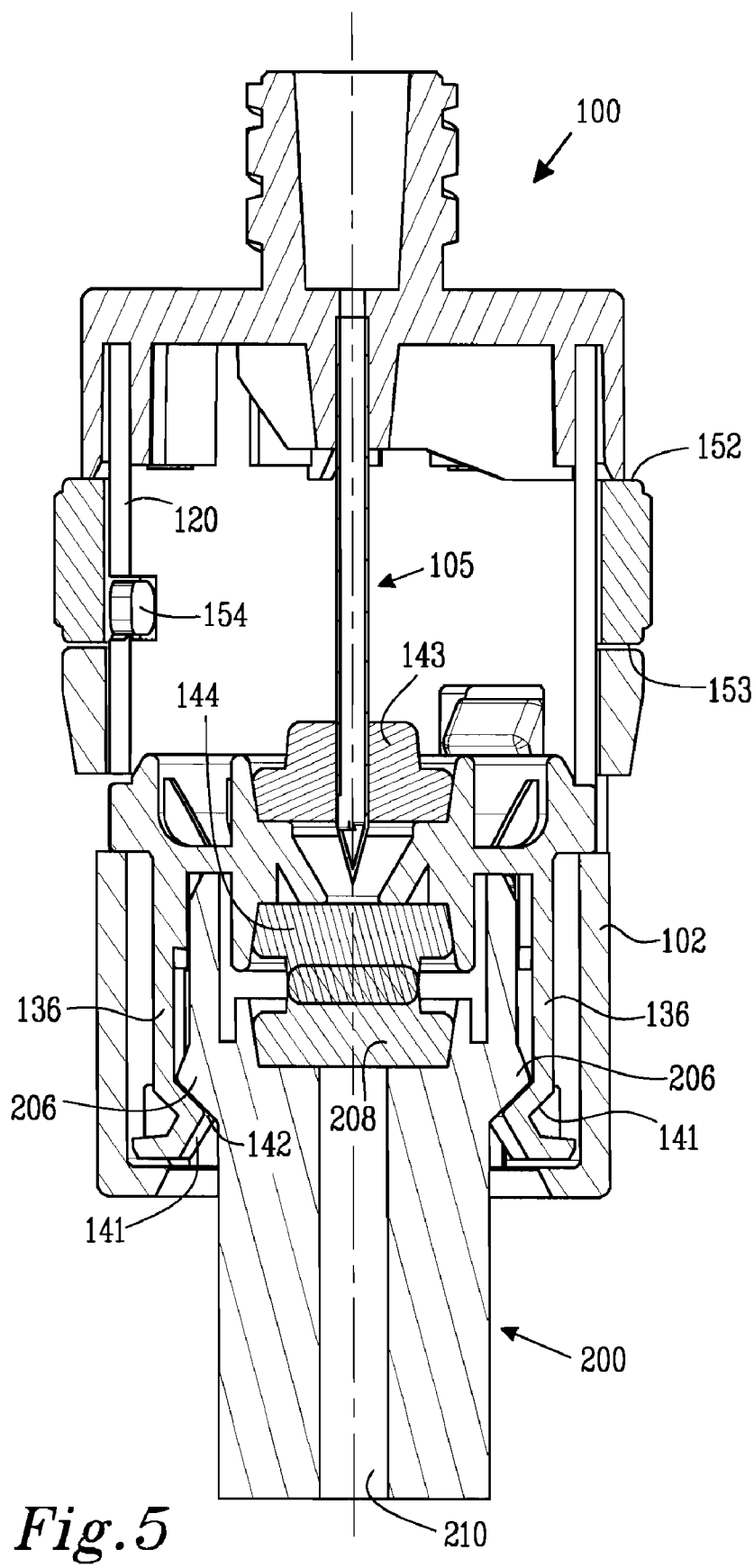
FIG. 5 shows a cross section of the female piercing member protection device and the male connection part after connection.

In FIG. 5, the female piercing member protection device 100 and the male connection part 200 assembly, and the cooperation there between, will be described. As mentioned above, the outer casing 102 can be turned between a first and a second position. In its second position, the locking flanges 136 of the connection member 101 are displaced from the apertures 114 of the outer casing 102. FIG. 5 is illustrated after turning the outer casing 102 to the second position.

As shown in FIG. 5, the male connection part 200 has been inserted into the female piercing member protection device 100. During insertion of the male connection part 200, the locking flanges 136 will slightly deform out in a radial direction, with respect to the longitudinal axis A, leaving space for the male connection part 200. The fold portion 141 is initially displaced by the transverse locking flange 206, but as the folding tip 142 has been passed, the locking flanges 136 will return to its normal position and thereby hold the male connection part 200 in a firm grip. As the outer casing 102 has been turned to its second position and the apertures 114 has been displaced from the locking flanges 136, the locking flanges 136 are substantially unable to deform out in a radial direction, with respect to the longitudinal axis A. The male connection part 200 is thereby effectively prevented from disconnecting from the connection member 101 and the female piercing member protection device 100, a secure and firm connection is thereby established, which protects a user from accidentally disconnect a fluid container during a fluid transfer and thereby expose the piercing member. The connection member 101 is still in the inactivated position, i.e. the piercing member has not yet penetrated the barrier members 144 and 208 to provide for a fluid communication.

Figure 6:
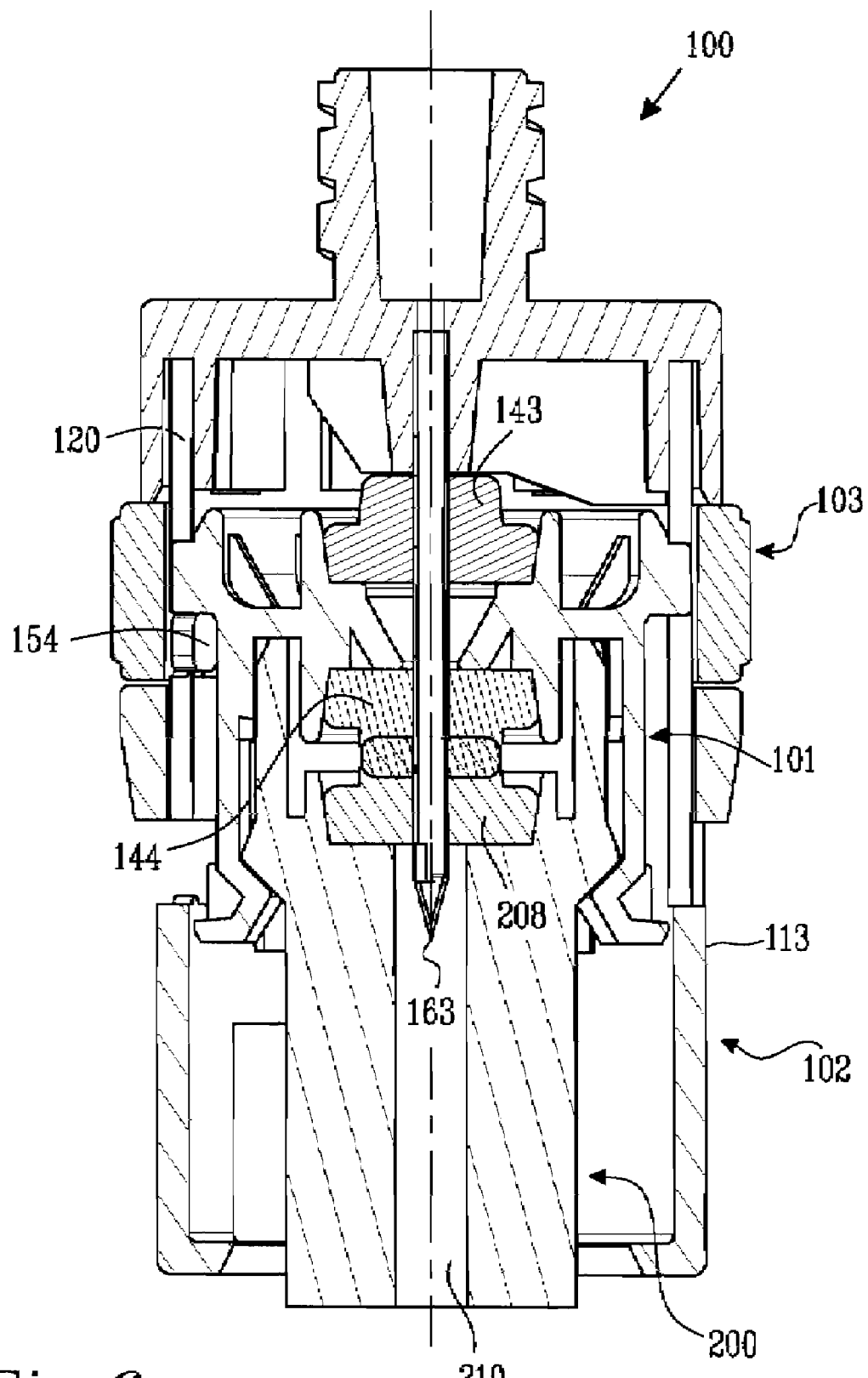
FIG. 6 shows a cross section of the female piercing member protection device and the male connection part in the activated position.

In FIG. 6 the male connection member 101 is positioned in the activated position. As can be seen both the first and the second barrier members 143, 144 are penetrated by the piercing member 105, the piercing tip 163 has reached inside the fluid communication channel 210 of the male connection part 200. The connection member 101 is now in the activated position.

Figure 7:
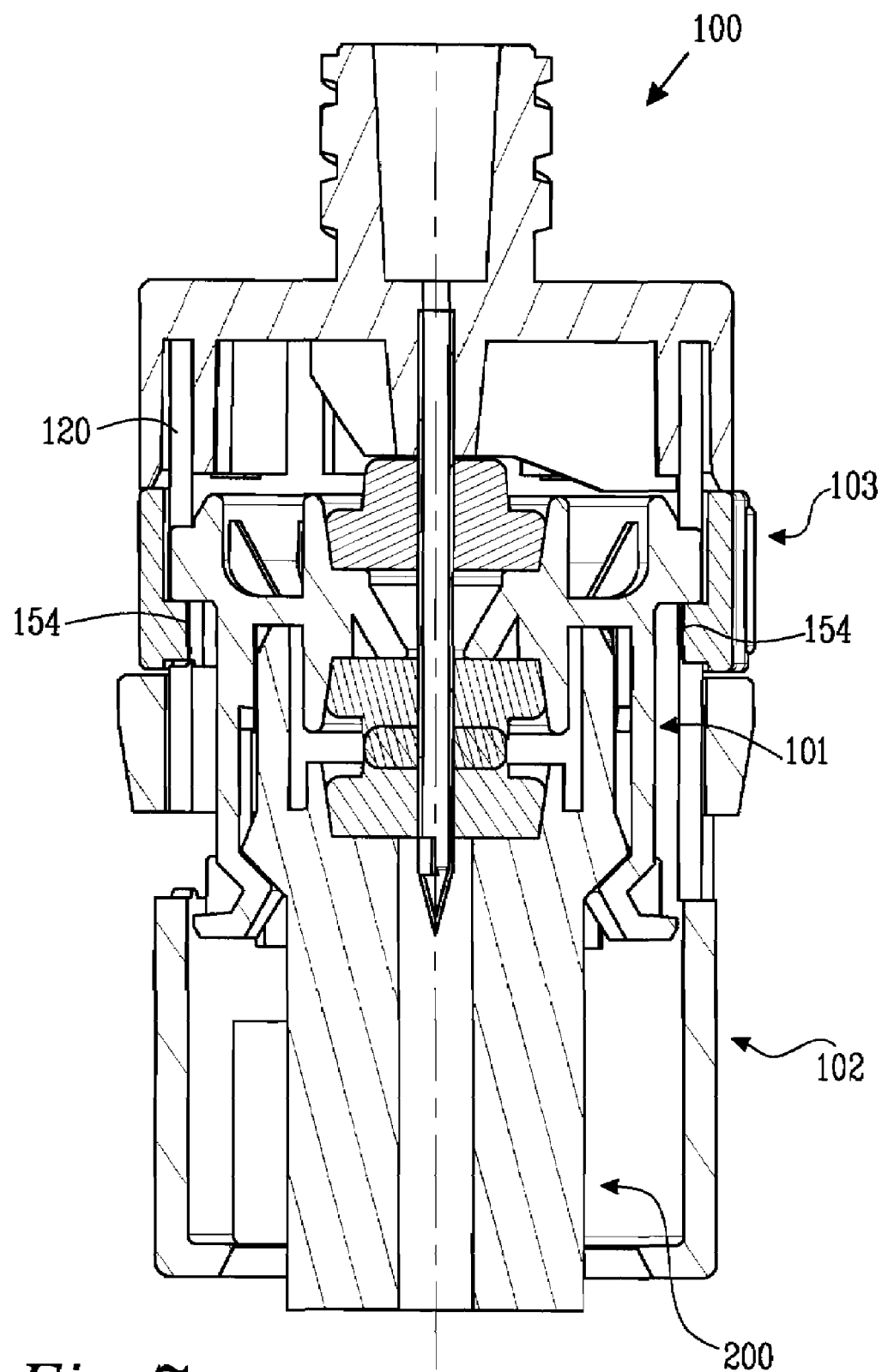
FIG. 7 shows a cross section of the female piercing member protection device and the male connection part in the activated position.

At this point, the locking ring 103 which is arranged circumferentially around the outer surface 113 of the outer casing 102 can be turned between a first position (as shown in FIGS. 5 and 6) to a second position (as shown in FIG. 7).

While the locking ring is in the unlocked position, the connection member 101 can slide between the activated position (as shown in FIG. 6) to the inactivated position (as shown in FIG. 5), however, when the locking ring 103 is turned to the locked position the connection member 101 is substantially unable to slide between the activated position (as shown in FIG. 6) to the inactivated position (as shown in FIG. 5). The locking mechanism of the locking ring 103 is provided by means of the locking protrusion 154, which has been described above.

The locking protrusion 154, which protrudes at least partly between the first and the second side 152, 153 from the inner surface 151 of the locking ring 103, runs in a part of the F-shaped channel system, which has been described above. More specifically, the locking protrusion 154 runs in the connection member locking channel 125 which extends perpendicular from the straight channel 120 of the outer casing 102. As can be seen in FIGS. 3, 5 and 6 the locking protrusion 154 is positioned in the connection member locking channel 125, but displaced from the straight channel 120 so as to permit the connection member 101 to reach its activated position. In FIG. 7 the locking ring 103 has been turned and the locking protrusion 154 has been moved to the connection member locking channel 125 so as to be positioned in the straight channel 120 and thereby effectively prevent the connection member 101 from being displaced from the activated position to the inactivated position.

The locking ring 103 or the locking protrusion 154 may further be arranged with a bias means (not shown), such as a spring, which will bias the locking protrusion 154 towards the straight channel 120 so as to provide for an automatic locking mechanism. If the locking protrusion 154 is properly formed, e.g. by making an angled surface towards the activation and inactivation positioning channel 126 of the outer casing 102, the locking protrusion 154 can be made to automatically lock the connection member 101 in the active position. During movement of the connection member 101 to the active position, the locking protrusion is pushed way, however, after the connection member 101 has passed the locking protrusion 154, the bias means bias the locking protrusion 154 back into the straight channel 120 and thereby effectively prevent the connection member 101 from returning to its inactive position. Hence the female piercing member protection device can be arranged with a manually second locking device, e.g. in which the user must turn the locking ring 103 himself to the locked position, or, an automatic second locking device, e.g. in which the locking ring 103 is automatically positioned in the locked position.

It is to be noted that the features described above may be combined in various ways, unless it is obviously inappropriate.

The invention claimed is:

1. A female piercing member protection device, having a longitudinal axis (A), for connection with a male connection part, said female piercing member protection device comprising:
    a piercing member;
    an outer casing having a first and a second end and an inner and an outer side, a connection member having a first and a second end, said connection member arranged to be rotatable between an activated position and an inactivated position, and at least partly enclosed in, said outer casing,
    further said outer casing arranged to be moved between a first and a second position,
    wherein when said outer casing is in its first position, the connection member is substantially locked from movement with respect to said outer casing and said piercing member, to said activated position along the longitudinal axis A and when said outer casing is in its second position the connection member is able to move with respect to said outer casing and said piercing member, to said activated position along the longitudinal axis A; and
    wherein the connection member comprises a deformable locking device that selectively engages said male connection part, wherein when said outer casing is in said second position, said deformable locking device is prevented from deformation by said outer casing so as to prevent disengagement of said male connection part, and wherein when said outer casing is in said first position, said deformable locking device is permitted to disengage with said male connection part.

2. The female piercing member protection device according to claim 1, wherein said connection member is arranged between said first and second end of said outer casing.

3. The female piercing member protection device according to claim 2, wherein said deformable locking device comprises at least one deformable locking flange.

4. The female piercing member protection device according to claim 3, wherein said deformable locking flange is an integrated part of the connection member.

5. The female piercing member protection device according to claim 3 or 4, wherein said outer casing comprises at least one aperture, and when said casing is in said first position, said aperture and said deformable locking flange is substantially aligned, so that said deformable locking flange can deform into said aperture during connection with said male connection part.

6. The female piercing member protection device according to claim 5, wherein when said outer casing is in said second position, said deformable locking flange is displaced from said aperture in said outer casing, so that said deformable locking flange is substantially unable to disengage from said male connection part.

7. The female piercing member protection device according to claim 5, wherein said connection member comprises at least two opposing deformable flanges.

8. The female piercing member protection device according to claim 7, wherein said connection member comprises at least four opposing deformable flanges.

9. The female piercing member protection device according to claim 3 or 4, wherein said inner side of said outer casing comprises a cavity, and when said casing is in said first position, said cavity and said deformable locking flange is substantially aligned, so that said deformable locking flange can deform into said cavity during connection with said male connector.

10. The female piercing member protection device according to claims 1, 2, 3 or 4, wherein said female piercing member protection device comprises a second locking device which can substantially lock said connection member from movement along said longitudinal axis (A), when said connection member is in said activated position.

11. The female piercing member protection device according to claim 10, wherein said second locking device comprises a locked position in which said connection member is substantially unable to slide along said longitudinal axis (A), and an unlocked position in which said connection member is substantially able to slide along said longitudinal axis (A).

12. The female piercing member protection device according to claim 11, wherein said second locking device comprises a manually locking device or an automatic locking device.

13. The female piercing member protection device according to claims 1, 2, 3 or 4, wherein said connection member comprises at least one barrier member.

14. The female piercing member protection device according to claim 13, wherein said connection member comprises two barrier members.

15. The female piercing member protection device according to claim 14, wherein two barrier members are arranged substantially parallel with respect each other and so as to intersect the longitudinal axis (A).

16. The female piercing member protection device according to claim 15, wherein said two barrier members are arranged so as to form a piercing tip protection chamber therebetween.

17. A method for connecting a female piercing member protection device according to claims 1, 2, 3 or 4, with a male connection part, said method comprising the steps of: connecting said connection member to said male connection by means of said deformable locking device, moving said outer casing with respect to said connection member from a first position, in which said female piercing member protection device is in an inactivated state and in which said connection member is substantially unable to slide to an activated position along said longitudinal axis (A), to a second position, in which said female piercing member protection device is in an inactivated state and in which said connection member is substantially able to slide along said longitudinal axis (A), to said activated state wherein when said outer casing is in said second position, said male connection part is substantially unable to disengage from said piercing member protection device, wherein said female piercing member protection device is thereafter activated by moving said connection member to said activated position relative to the outer casing and with respect to the piercing member.

18. The method for connecting a female piercing member protection device with a male connection part according to claim 17, wherein said connection member can be substantially locked in said activated position by means of a locking ring arranged around the outer casing.

19. The method for connecting a female piercing member protection device with a male connection part according to claim 17, wherein said deformable flange provides a snap-on connection.

* * * * *